US007953491B1

(12) United States Patent
Hartley

(10) Patent No.: US 7,953,491 B1
(45) Date of Patent: *May 31, 2011

(54) AUTO-REFERENCING MIXED-MODE PHASE LOCKED LOOP FOR AUDIO PLAYBACK APPLICATIONS

(75) Inventor: Lee F Hartley, Valencia, CA (US)

(73) Assignee: Advanced Bionics, LLC, Valencia, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/861,746

(22) Filed: Aug. 23, 2010

Related U.S. Application Data

(62) Division of application No. 11/381,716, filed on May 4, 2006, now Pat. No. 7,787,957, which is a division of application No. 10/218,614, filed on Aug. 13, 2002, now Pat. No. 7,155,289.

(60) Provisional application No. 60/313,227, filed on Aug. 17, 2001.

(51) Int. Cl.
*A61N 1/36* (2006.01)
(52) U.S. Cl. ........................................................ 607/57
(58) Field of Classification Search ............... 607/55–57
See application file for complete search history.

(56) References Cited

U.S. PATENT DOCUMENTS 7,155,289 B1 * 12/2006 Hartley ........................... 607/57
* cited by examiner

*Primary Examiner* — George R Evanisko
(74) *Attorney, Agent, or Firm* — Bryant R. Gold

(57) ABSTRACT

Audio streaming is made available throughout the signal processing path of the speech processor of a cochlear implant or other audio signal processor. Audio streaming comprises the digitally phase locked playback of a real time n-bit digital audio stream, where n may be a large number, e.g., 8, 12, 16, 24 or 32, that emanates (unsolicited) from an operating speech processor. A number of sample points are made available long the processing chain of a digital signal processor (DSP) used within the speech processor of the cochlear implant. Audio streaming may occur at any sample point. The signal at a selected sample point may be selectively monitored in order to allow appropriate diagnostics to be performed. Audio streaming utilizes an auto-referencing mixed-mode phase locked loop. Such phase locked loop processes an asynchronous stream of digital audio samples that arrive at a designated location, e.g., a selected sample point, at a consistent, but unknown, average rate. Once the stream of asynchronous audio samples are received, the average sample rate is extracted, and a local clock is generated at the average frequency. The incoming audio streaming samples are then re-synchronized with the local clock. in order to allow digitally phase locked playback of the audio stream.

9 Claims, 5 Drawing Sheets

AUTO-REFERENCING MIXED-MODE PHASE LOCKED LOOP FOR AUDIO PLAYBACK APPLICATIONS

The present application is a Divisional of U.S. patent application Ser. No. 11/381,716, filed May 4, 2006, to be issued as U.S. Pat. No. 7,787,957 on Aug. 31, 2010; which application is a Divisional of U.S. Pat. No. 7,155,289, issued Dec. 26, 2006; which application claims the benefit of U.S. Provisional Application Ser. No. 60/313,227, filed Aug. 17, 2001, which application (including its Appendix A) is incorporated herein in its entirety.

BACKGROUND OF THE INVENTION

The present invention relates to cochlear implants, and more particularly to an auto-referencing mixed-mode phase locked loop for audio playback applications, such as occurs when performing audio streaming diagnostics relative to the performance of a bionic ear implant.

A new generation of cochlear implants, commonly referred to as a "bionic ear" implant, has recently been introduced to the cochlear implant community. A representative bionic ear implant is the CII Bionic Ear™ cochlear implant system introduced by Advanced Bionics Corporation, of Sylmar Calif. A bionic ear implant is capable of delivering electrical stimulation to a patient at rates and resolutions which surpass that of conventional cochlear implants.

With any cochlear implant, there is a continual need to know how the implant is functioning and what the patient using the cochlear implant is hearing. That is, patients may report hearing "noise" or "distortion" in a particular channel, and may use such terms as "cracking", "popping" "tickling", "gurgling", "rattling" etc. to describe such noise. It would thus be helpful if the clinician or other interested parties, e.g., parents or teachers of young children who have been fitted with a cochlear implant, could actually "hear" what the patient is hearing. Disadvantageously, there has not been a diagnostic tool available that has allowed such listening.

In order to "listen in" to what a cochlear implant patient may be hearing, it is necessary to process an asynchronous stream of digital audio samples that arrive at a receiver location at a consistent, but unknown, average rate. Once the stream of asynchronous audio samples are received, there is a need for a way of extracting the average sample rate, generating a local clock at the average frequency, and re-synchronizing the incoming audio samples to that clock. With such re-synchronized clock, it would then be possible to recreate the stream of audio data so that one can listen to it, or analyze it for other diagnostic purposes.

SUMMARY OF THE INVENTION

The present invention addresses the above and other needs by providing audio streaming throughout the signal processing path of the speech processor of a cochlear implant. Audio streaming comprises the digitally phase locked playback of a real time n-bit digital audio stream, where n may be a large number, e.g., 8, 12, 16, 24 or 32, that emanates (unsolicited) from an operating speech processor.

In accordance with one aspect of the invention, a number of sample points, or tap-points, are made available along the processing chain of the digital signal processor (DSP) used within the speech processor of a cochlear implant system. Audio streaming may occur at any sample point. That is, the signal at a selected sample point may be monitored, using the audio streaming principles of the present invention, in order to allow appropriate diagnostics to be performed. For example, one way to validate whether a patient's microphone is working properly is to "listen" to the raw microphone signal. Similarly, if a patient reports noise or distortion in a particular channel, then "listening" to the automatic gain control (AGC) output or specific channel filter outputs can help the clinician diagnose the nature of the noise or distortion as well as its source.

Audio streaming thus involves processing an asynchronous stream of digital audio samples that arrive at a designated location, e.g., a selected sample point, at a consistent, but unknown, average rate. Once the stream of asynchronous audio samples are received, the average sample rate must be extracted, and a local clock is then generated at the average frequency. The incoming audio streaming samples are then re-synchronized with the clock in order to allow digitally phase locked playback of the audio stream.

One of the advantages of the present invention is that it allows for the objective evaluation of different speech processing algorithms.

Another advantage of the invention is that it allows for both qualitative as well as quantitative analysis of various points in the DSP's audio data flow path.

It is a feature of the invention to provide a way whereby a clinician, teacher or parent may "listen" to what a cochlear implant patient is hearing.

It is another feature of the invention to provide for the extraction of a stable clock from an asynchronous stream of audio samples. Such stable clock advantageously allows accurate playback of digital audio at arbitrary sample rates and with no prior knowledge of the sample rates.

It is a further feature of the invention to provide a platform through which precision analysis and verification of the entire audio signal processing path within a cochlear implant system is made possible.

BRIEF DESCRIPTION OF THE DRAWINGS AND APPENDIX

The above and other aspects, features and advantages of the present invention will be more apparent from the following more particular description thereof, presented in conjunction with the following drawings wherein.

Figure 1:
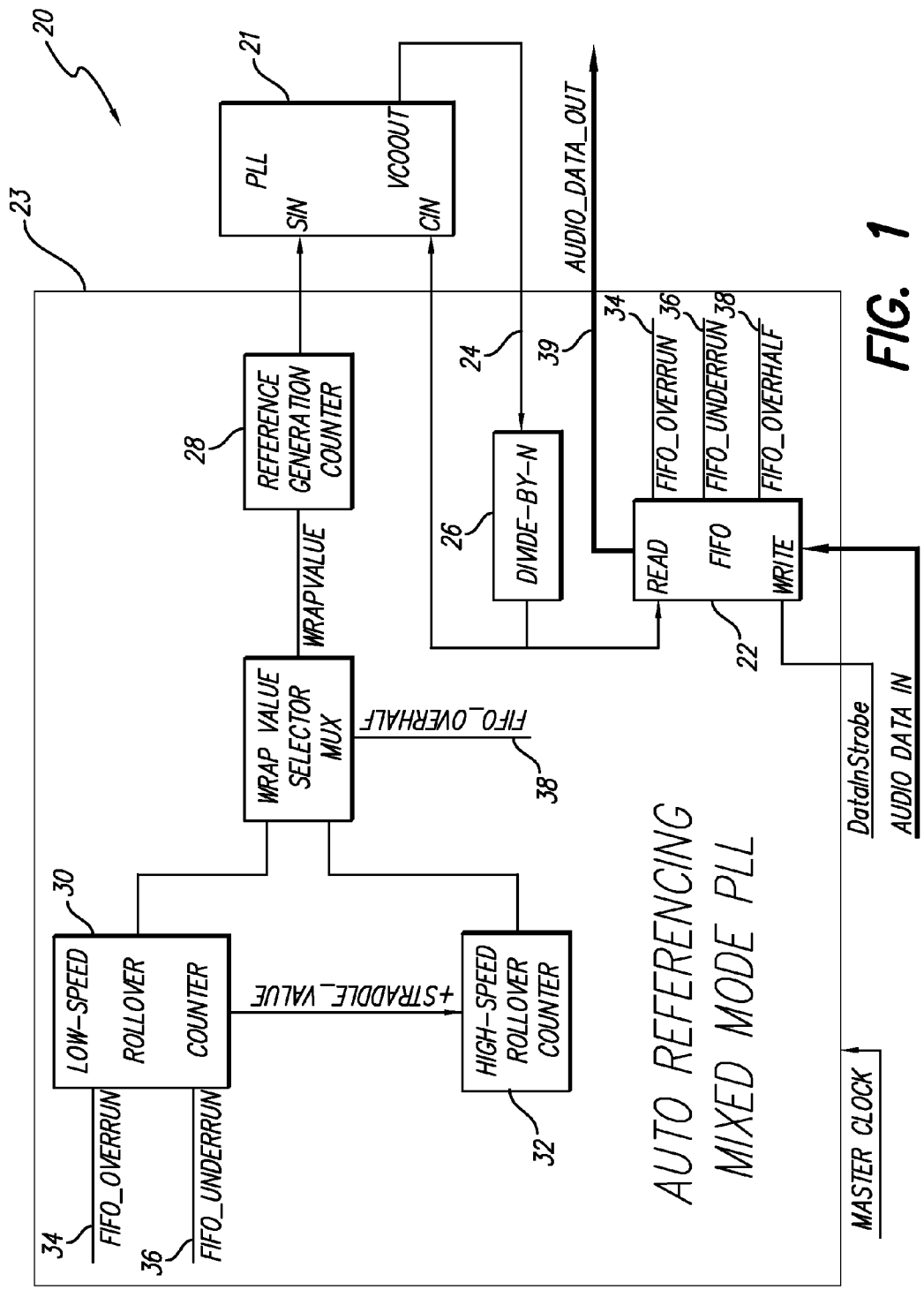
FIG. 1 is a functional block diagram of an auto-referencing mixed-mode phase locked loop (PLL) used to extract a stable clock from an incoming asynchronous digital audio sample stream.

Additional information regarding a programming system for use with a bionic ear implant, including the use of audio streaming diagnostics with such implant, are presented in Appendix A of the above-referenced provisional application (Ser. No. 60/313,227, filed Aug. 17, 2002), previously incorporated herein by reference.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention.

An auto-referencing mixed-mode phase-lock loop (PLL) structure 20, at the heart of the audio streaming of the present invention, is shown in FIG. 1. Such structure includes an auto-referencing mixed-mode PLL circuit 23 (which includes several counters, a FIFO, and other circuitry as described below) and a PLL chip circuit 21. The PLL chip circuit 21, e.g., a standard 74HC4046 PLL chip available from numerous semi-conductor chip manufacturers, such as Motorola or Texas Instruments, or an equivalent PLL chip circuit, is assisted by an external first-in-first-out (FIFO) buffer circuit 22. The FIFO 22 functions as a queue to implement a self-adaptive, stable audio playback system. The PLL chip 21 is used in it's positive edge phase comparator mode whereby the device's internal voltage controlled oscillator (VCO) is fed to the low-pass filtered output of its digital phase comparator. The resultant VCO output, on signal line 24, is proportional to this phase difference and at perfect coincidence of phase and frequency, and the VCO output is stable at N times (x) the input signal's frequency. A digital feedback divider 26 divides the VCO output by N. The divider 26 is generated external to the PLL chip 21 and allows for clock multiplication if N>1.

In a preferred embodiment, the PLL structure described above is assisted by the auto-referencing mixed-mode PLL circuit 23 that generates the reference target to the PLL chip 21 and adjusts that input in response to the dynamic utilization of the local FIFO 22. The system maintains three digital counters, (1) a reference generation counter 28, (2) a low-speed rollover counter 30, and (3) a high-speed rollover counter 32. Out of reset, the low-speed rollover counter 30 is reset to it's maximum value and the reference generation counter begins to count from zero at the master clock frequency. (The master clock is a clock several orders faster, in this case 30 MHz, than the target playback frequency, 10-40 kHz). The high-speed rollover counter 32 is always maintained at a value (the Straddle_Depth) less than the low-speed rollover counter 30.

In operation, in the absence of incoming audio data, the FIFO 22 remains empty and the reference generation counter 28 resets to zero when the low-speed rollover count value is reached. This is the first stable operating point. As audio data samples begin to arrive, they are queued up in the local FIFO 22 and a depth counter (internal to the FIFO 22) tracks the number of samples held. Once ½ full, the FIFO 22 is deemed to be "primed" and playback is enabled. With data asynchronously arriving into the FIFO 22 at the audio sampling rate, and synchronously being removed from the FIFO 22 at the phase locked playback rate, the goal of the present embodiment is to dynamically adjust the playback rate until the values of the low-speed rollover counter 30 and the high-speed rollover counter 32 straddle the number of cycles of the master clock in one period of the audio sampling rate (i.e. the ideal target playback rate). Under such conditions, the FIFO utilization will remain stable at approximately the ½ full condition.

To achieve the above-described FIFO regulation, the following internally generated signals are generated and utilized: FIFO Overrun (on signal line 34), FIFO Underrun (on signal line 36), and FIFO Over Half (on signal line 38). The first two signals indicate significant mismatch between playback and sampling rates and are used to adjust the low/high-speed rollover counter values. A FIFO Overrun signal (which indicates the arrival of an audio sample into an already full FIFO) indicates the rate of incoming audio samples far exceeds the maximum playback rate, so the low-speed roll-over counter is decremented each time a FIFO overrun signal occurs. A FIFO Underrun signal (which indicates an attempt to read a byte from the FIFO in which there are no stored audio samples) indicates the rate of incoming audio samples falls far short of the minimum playback rate, so the low-speed rollover counter is incremented and the FIFO "primed" signal is de-asserted. The FIFO Over Half signal is used to toggle between the low/high-speed rollover counter values as the threshold at which the reference generation counter resets to zero and the input reference to the PLL chip 21, e.g., a 74HC4046 chip, is inverted.

When the FIFO Over Half signal is TRUE, the high-speed rollover counter is selected and the input to the external PLL 21 (e.g., a 74HC4046 chip) is increased in frequency slightly such that it is just over the audio sampling rate. When the FIFO Over Half signal is FALSE, the low-speed rollover counter is selected and the input to the external PLL chip 21 is decreased in frequency slightly such that it is just under the audio sampling rate. In this way, the FIFO is maintained at or near ½ full and the average output of the PLL chip 21 settles upon the target audio sampling rate.

In such manner as described above, any rate of incoming audio data may be locked onto and played back at the intended sampling rate. There is no dependency on the source system to also provide a reference clock, or to otherwise inform the hybrid PLL system of the actual rate. In the event that the incoming audio sample rate is changed, equilibrium of the above system will be disrupted and a new playback rate will be arrived at through the system's response to overrun and underrun conditions.

Figure 2:
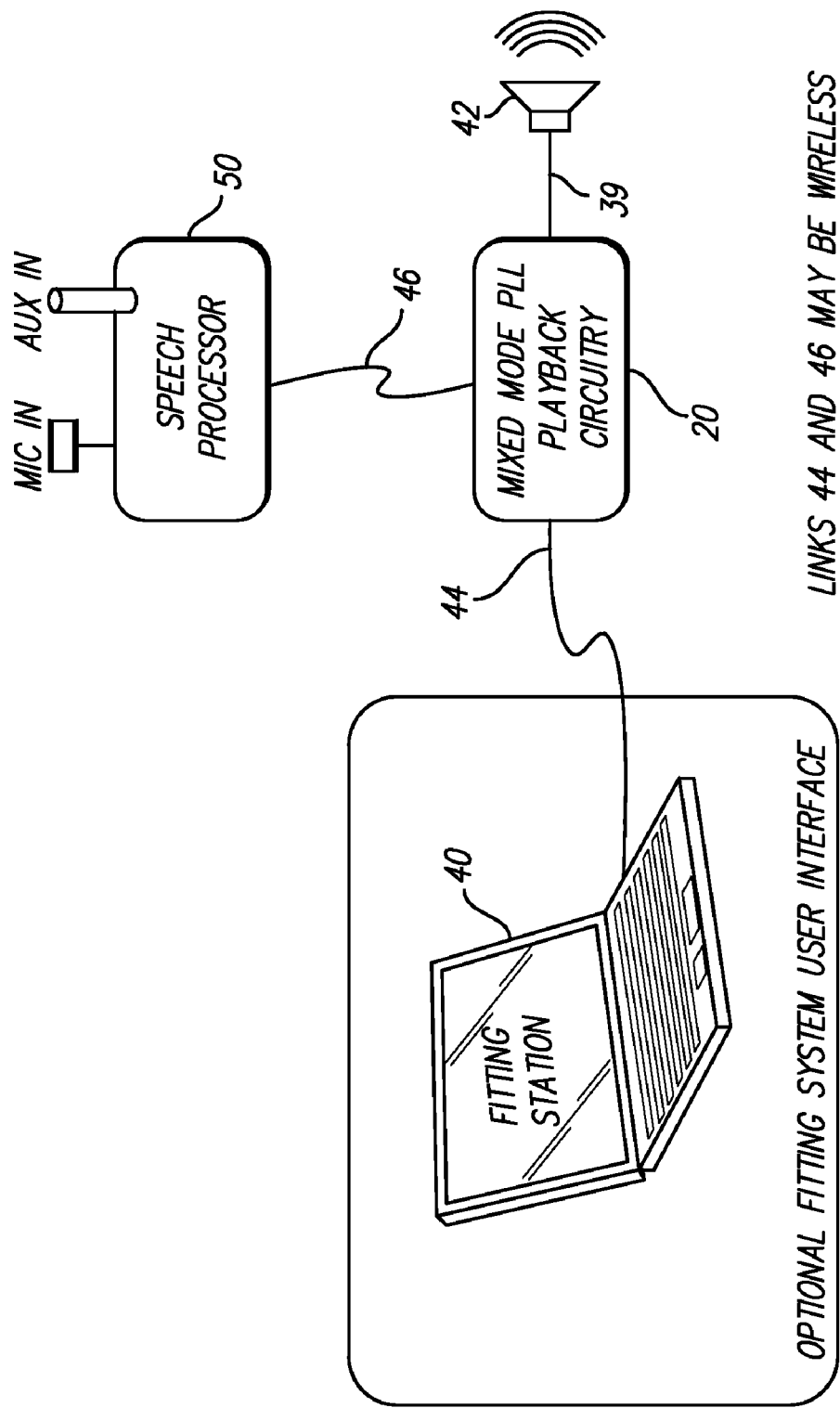
FIG. 2 shows how the mixed mode PLL of FIG. 1 interfaces with a clinician fitting system used to fit a bionic ear implant.

Turning next to FIG. 2, one preferred manner of using the auto-referencing mixed-mode PLL 20 to provide audio streaming is depicted. A speaker 42 is coupled to the Audio_Data_Out signal line 39 of the PLL 20. A PC-based clinician fitting system 40 is linked to the mixed-mode PLL 20 via communication link 44. Similarly, a speech processor 50 from a cochlear implant system is linked to the mixed-mode PLL 20 via communication link 46. The links 44 and 46 may be wired or wireless. The communications between the PC-based fitting system 40 and speech processor 50 with the mixed-mode PLL 20 are maintained in real time audio streaming by way of a robust packet-based communications protocol and accompanying hardware support. Such support segregates streaming audio data from PC-bound packet data when both arrive over a high speed serial link.

In the preferred embodiment, audio streaming is accessed from a miscellaneous commands menu that appears on the programming screen of the PC-based fitting system 40. Users simply select the "probe point" to which they want to listen. The speech processor of the cochlear implant, e.g., the speech processor of the CII Bionic Ear implant, then maps the chosen probe point to the physical address in the DSP memory from which the target originates. Data from this address then begins streaming back to the interface hardware, where the mixed-mode PLL 20 is located, over link 44, for playback at a programmed-determined rate.

Advantageously, in addition to being able to "listen in" on what the patient is hearing through his or her bionic ear implant during a fitting session, the audio streaming feature provides a valuable diagnostic tool for investigating a wide range of advanced research and development efforts. For example, the audio streaming feature of the present invention may be used to investigate the following items, which list is not exhaustive: (a) audio filtering; (b) dynamic analysis of automatic gain control systems; (c) anti-alias decimation; (d) audio path gain analysis; (e) noise floor characterization; (f) measurement of microphone sensitivity; (g) telephony performance; (i) total harmonic distortion analysis; (j) frequency response analysis; and (k) transient analysis.

Figure 3:
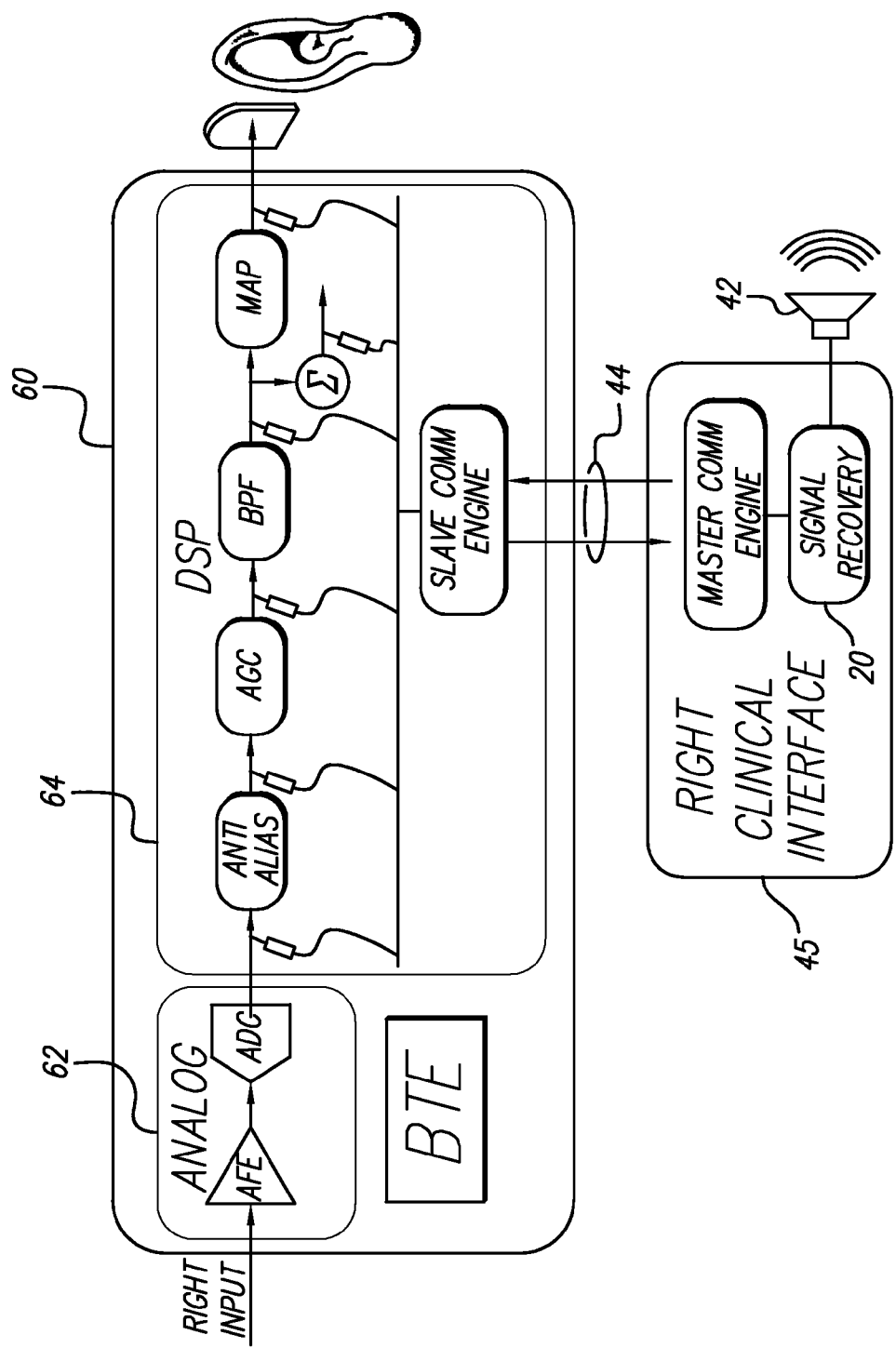
FIG. 3 illustrates how audio streaming may be used to "listen in" on what a cochlear implant patient may be hearing.

Next, with reference to FIG. 3, the manner of using audio streaming monaurally is illustrated. A behind-the-ear (BTE) speech processor 60 provides an audio signal path that includes analog front end circuitry 62 and DSP circuitry 64. A clinician interface 45 houses the mixed-mode PLL 20 in order to perform signal recovery, and the appropriate communications circuitry for establishing the communications link 44 with the BTE. Advantageously, it is possible for any DSP memory address to be streamed out. For practical purposes, however, a predefined set of relevant tap-points is made available to clinicians through the clinician interface 45. Such tap points may include, e.g., AGC input, AGC output, Channel m Output (where m represents the number of available channels, e.g., from 1 to 16), anti-alias output, map output, and the like.

Figures 1, 4:
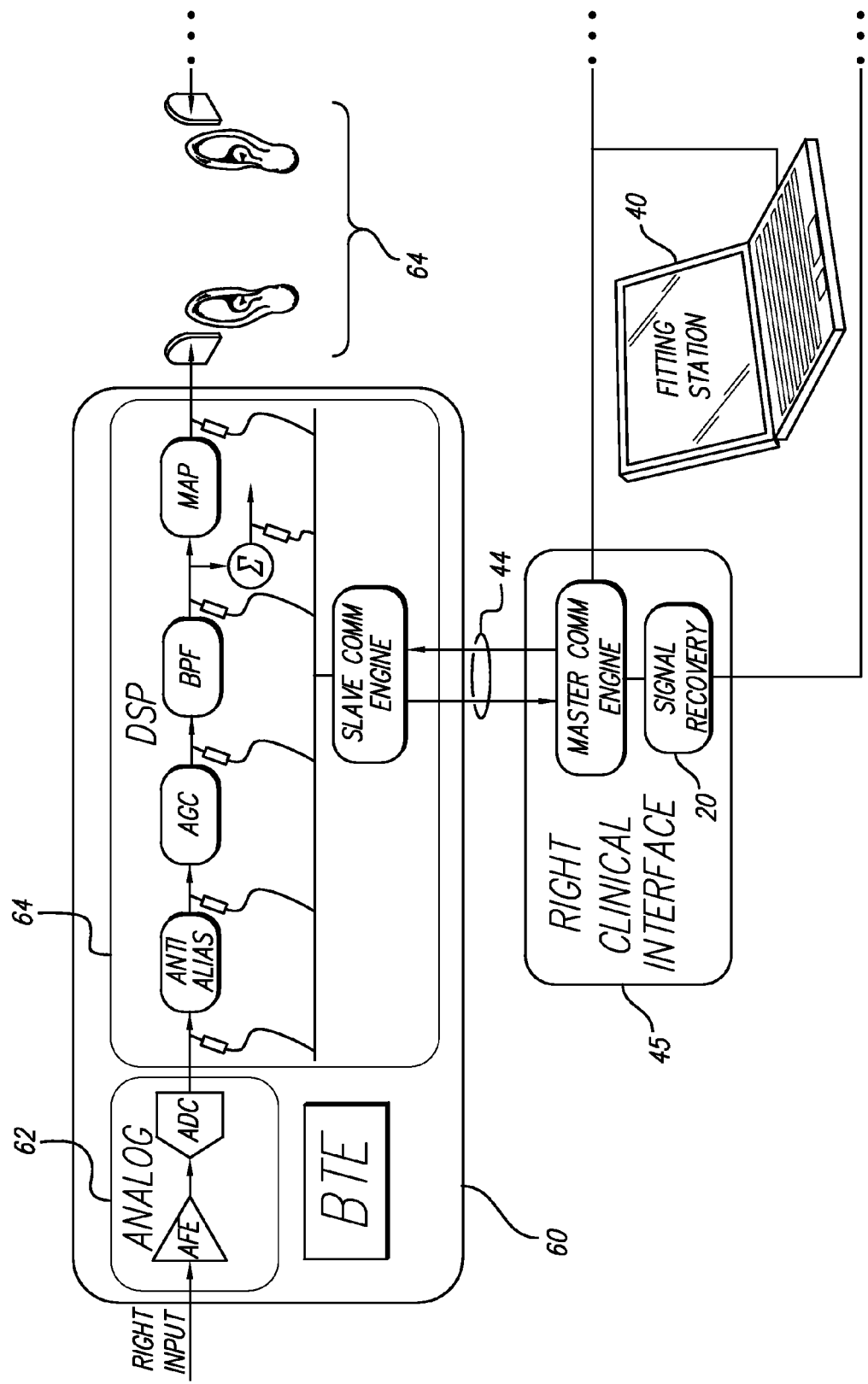
FIG. 4 illustrates use of audio streaming for a binaural patient.
Figures 2, 4:
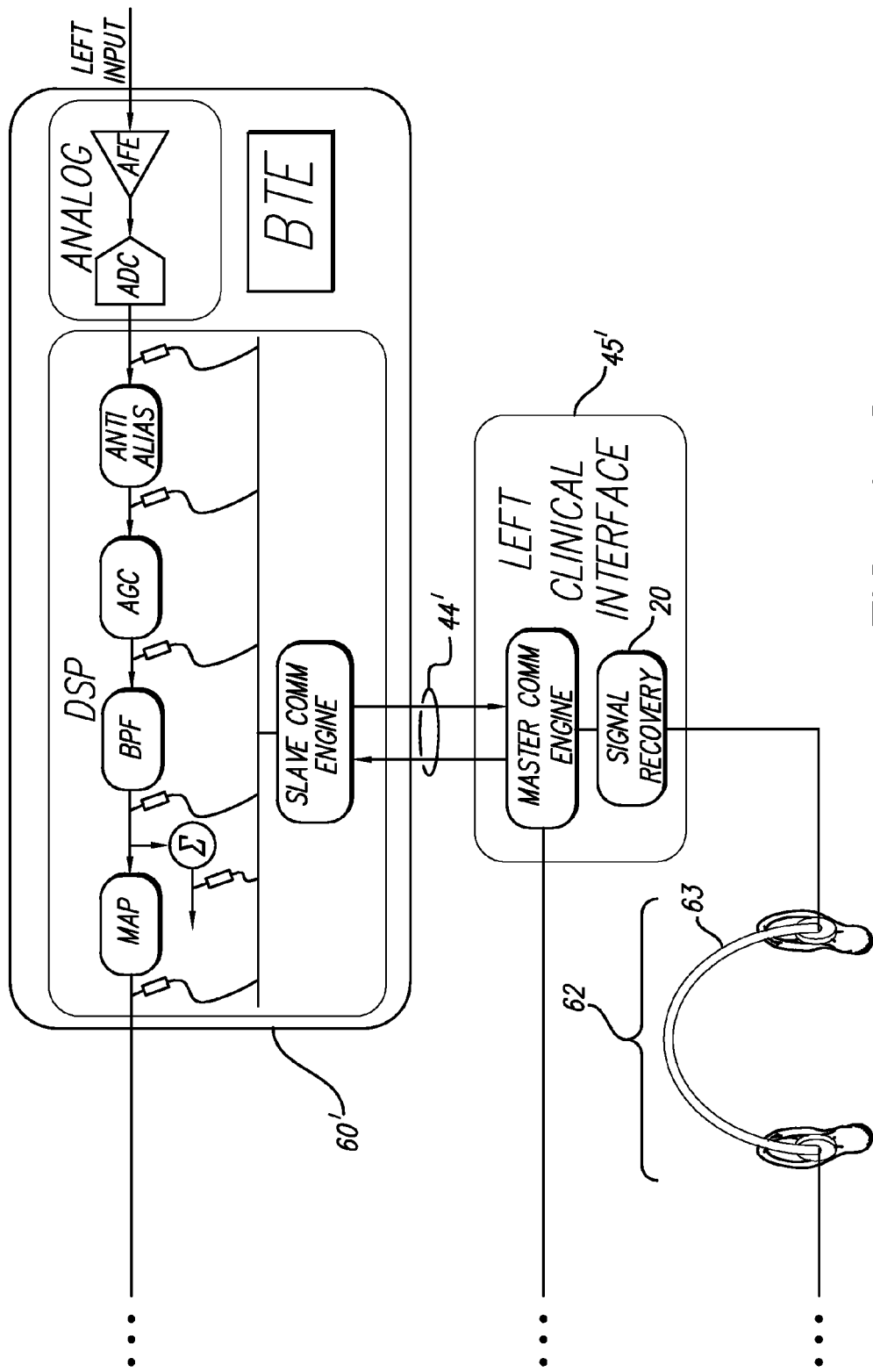

FIG. 4 illustrates how the invention is used for binaural fittings. (Note: FIG. 4 is split between two sheets of figures, FIGS. 4-1 and 4-2. The two figures placed side-by-side, with FIGS. 4-1 on the left, and FIGS. 4-2 on the right, comprise FIG. 4.) As seen in FIG. 4, the binaural system includes two BTE's, a right BTE 60 and a left BTE 60'. Each is connected to its own interface circuitry 45 or 45' via suitable communication links 44 or 44'. A auto-referencing mixed-mode PLL 20 is included within each interface circuit. A clinician 62 may "listen" to what a patient 64 is hearing through a set of ear phones 63, or may monitor other tap points in either the left or right audio signal paths, as desired. Thus, it is seen that audio streaming offers clinicians access to pertinent information related to, intra alia, directional hearing, balancing and contra-lateral channel allocation.

While the invention herein disclosed has been described by means of specific embodiments and applications thereof, numerous modifications and variations could be made thereto by those skilled in the art without departing from the scope of the invention set forth in the claims.

What is claimed is:

1. An audio streaming playback system comprising:
   an audio processor for processing an audio signal stream, the audio processor including analog front end circuitry and digital signal processing circuitry connected to each other;
   a multiplicity of tap points within the digital signal processing circuitry whereat the signal stream being processed is adapted to be sampled; and
   an auto-referencing mixed-mode phase locked loop system selectively coupled to at least one of the multiplicity of tap points, said phase locked loop system including means for allowing signal stream passing through the digital signal processing circuitry to be asynchronously received by the phase locked loop system at a sample rate, and played backed at a synchronous rate that is automatically dynamically adjusted to approach the sampling rate.

2. The audio playback system of claim 1 wherein the digital signal processing circuitry includes, in series, anti-aliasing circuitry, automatic gain control (AGC) circuitry, bandpass filter (BPF) circuitry, and mapping circuitry, and wherein one of the multiplicity of tap points exists at the input of the anti-aliasing circuitry, at the interface between the anti-aliasing circuitry and the AGC circuitry, at the interface between the AGC circuitry and the BPF circuitry, at the interface between the BPF circuitry and the mapping circuitry, and at the output of the mapping circuitry.

3. The audio playback system of claim 1 further including a wired connection and wherein the auto-referencing mixed-mode phase locked loop system is coupled to the selected tap point via the wired connection.

4. The audio playback system of claim 1 further including a wireless connection and wherein the auto-referencing mixed-mode phase locked loop system is coupled to the selected tap point via the wireless connection.

5. The audio playback system of claim 1 wherein the auto-referencing mixed-mode phase locked loop system comprises:
   a phase-locked loop (PLL) input signal;
   a phase-locked loop (PLL) circuit that receives the PLL input signal and that generates a VCO-Out signal having a rate that is locked to the PLL input signal;
   a first-in first-out (FIFO) circuit that receives the audio signal stream asynchronously at an audio sampling rate, thereby creating audio data held within the FIFO circuit, and wherein the audio data is synchronously removed from the FIFO at a phase locked playback rate determined by the VCO-Out signal of the PLL circuit, and wherein the FIFO circuit generates a FIFO_Overrun signal when full, a FIFO_Underrun signal when less than ½ full, and a FIFO_Overhalf signal when more than ½ full;
   a low-speed rollover counter that is decremented by the FIFO_Overrun signal and incremented by the FIFO_Underrun signal;
   a high-speed rollover counter that maintains a count value related to, but greater than, the value of the low-speed rollover counter; and
   a wrap value selector multiplexer circuit that selects either the contents of the low-speed rollover counter or the contents of the high-speed rollover counter as a function of the FIFO_Overhalf signal;
   wherein when the FIFO Overhalf signal is TRUE, the high-speed rollover counter is selected as the PLL input signal, thereby causing the frequency of the VCO-Out signal generated by the PLL circuit to increase slightly so that it is just over the audio sampling rate; and
   wherein when the FIFO Overhalf signal is FALSE, the low-speed rollover counter is selected as the PLL input signal, thereby causing the frequency of the VCO-Out signal generated by the PLL circuit to decrease slightly so that it is just under the audio sampling rate;
   wherein he FIFO is maintained at or near ½ full and the VCO-Out signal generated by the PLL circuit has an average rate that settles upon the audio sampling rate.

6. The audio playback system of claim 5 further including a fitting station coupled to the auto-referencing mixed-mode phase locked loop system that facilitates selecting a desired one of the multiplicity of tap points within the auto-referencing mixed-mode phase locked loop system.

7. The audio playback system of claim 6 wherein the fitting station comprises a personal computer processing system having a display screen on which a selection menu is adapted to be displayed.

8. The audio playback system of claim 5 wherein the audio processor comprises a cochlear implant speech processor of a cochlear implant system.

9. The audio playback system of claim 8 wherein the cochlear implant speech processor comprises a behind-the-ear (BTE) speech processor of the cochlear implant system.

* * * * *